United States Patent [19]

Schoen et al.

[11] Patent Number: 4,990,291

[45] Date of Patent: Feb. 5, 1991

[54] METHOD OF MAKING LIPID TUBULES BY A COOLING PROCESS

[75] Inventors: Paul E. Schoen, Alexandria, Va.; Paul Yager, Seattle, Wash.; Joel M. Schnur, Burke, Va.

[73] Assignee: The United States of America as represented by the Secretary of the Navy, Washington, D.C.

[21] Appl. No.: 161,934

[22] Filed: Feb. 29, 1988

Related U.S. Application Data

[63] Continuation-in-part of Ser. No. 852,596, Apr. 15, 1986, abandoned.

[51] Int. Cl.$^5$ .................. A61K 9/127; B01J 13/18
[52] U.S. Cl. ........................... 264/4.7; 264/4.3; 424/450; 514/832; 514/885; 522/171
[58] Field of Search ............... 264/4.4, 4.7; 424/450; 436/829; 522/171

[56] References Cited

U.S. PATENT DOCUMENTS

| | | | |
|---|---|---|---|
| 4,089,801 | 5/1978 | Schneider | 424/450 X |
| 4,260,515 | 4/1981 | Sliwka | 264/4.3 |
| 4,394,372 | 7/1983 | Taylor | 514/788 X |
| 4,448,765 | 5/1984 | Ash et al. | 264/4.7 X |
| 4,485,045 | 11/1984 | Regen | 264/4.7 X |

OTHER PUBLICATIONS

Yager et al.: "Formation of Tubules by a Polymerizable Surfactant", *Mol. Cryst. Liq. Cryst.*, 1984, vol. 106, pp. 371-381.
Yager et al.: "Structure of Lipid Tubules Formed from a Polymerizable Lecithin", *Biophysical Journal*, vol. 48, 1985, pp. 899-906.
Singh et al.: "Polymerized Diacetylenic Phosphatidyl Choline Vesicles: Synthesis and Characterization", *Polymer Preprints*, vol. 26, No. 2, pp. 184-185, (Sep. 1985).
Schnur et al.: "Reversible Thermochromism in Photopolymerized Phosphatidyl Choline Vesicles", *Polymer Preprints*, vol. 26, No. 2, pp. 186-187, (Sep. 1985).
Singh et al.: "Synthesis and Characterization of Positional Isomers of 1,2-Bishepacosadiynoyl Phosphatidyl Cholines", *Abstracts of Sixth Int. Symp. on Surfactants in Solution*, New Delhi, India, p. 193 (Aug. 18-22, 1986).
Singh et al.: "Tubule Formation by Heterobifunctional Polymerizable Lipids: Synthesis and Characterization", *Polymer Preprints*, vol. 27, (Sep. 1986).

*Primary Examiner*—Richard D. Lovering
*Attorney, Agent, or Firm*—Thomas E. McDonnell; Barry A. Edelberg

[57] ABSTRACT

Diacetylinic phosophocholines have distinctly different endothermic and exothermic transition temperatures. Lipid tubules are formed by hydrating a diacetylinic phosphocholine at a temperature above its endothermic transition temperature. The hydrated lipid is then cooled slowly to a formation temperature 1° to 10° C. below the exothermic transition temperature to form tubule structures. The tubules structures can be polymerized to form permanent tubules. The tubules can be used in the same manner as a liposome vesicle or they can be metal coated for a variety of applications.

12 Claims, 3 Drawing Sheets

METHOD OF MAKING LIPID TUBULES BY A COOLING PROCESS

CROSS-REFERENCE

This application is a Continuation-In-Part of Application 852,596 filed Apr. 15, 1986 and now abandoned.

BACKGROUND OF THE INVENTION

1. Field of the Invention

This invention relates to a method of forming tubules from diacetylenic phospholipids and to the tubule structures formed by the method. Particularly, this invention pertains to a method of forming tubules by slowly cooling multilamellar vesicles through the liquid crystalline gel point to a formation point 1-10° C. below the gel phase transition temperature.

2. Description of the Prior Art

In recent years there has been an increasing interest in the use of synthetic lipid structures for a variety of applications including model membranes, immunological adjuncts, drug carriers, artificial blood substitutes and the like. The preparation of liposomes provide a practical and effective means for encapsulating liquids and solids. Liposomes are particularly useful for administrating biologically active substances into living organisms. The liposome protects substances from destruction or inactivation by bodily processes or by organisms until the substance reaches the desired reaction site in the body.

Liposomes are widely described in the literature and their general structure and methods for preparation are well known. Basically, liposomes are spheroidal structures having a lipid membrane which encapsulates materials.

Methods of preparing liposomes and encapsulates material in liposomes are described in such references as U.S. Pat. No. 4,089,801 to Schneider which discloses synthetic liposomes containing biologically active substances prepared by submitting the solvent and lipids to ultrasonic vibrations, U.S. Pat. No. 4,448,765 to Ash et al. which discloses unilamellar liposomes stabilized by the incorporation of a polymerizable lipid into the liposome membrane and U.S. Patent No. 4,133,874 to Miller et al. which discloses synthetic liposomes containing hemoglobin which functions as a blood substitute. The Miller liposomes are also prepared by ultrasonic energy. Szoka et al., provides a general review for liposome synthesis in *Preparation of Unilamellar Liposomes of Intermediate Size (0.1-0.2 m) By A Combination of Reverse Phase Evaporation and Extrusion Through Polycarbonate Membranes*, Biochimica et Biophysics Acta, 601 (1980) 5590571.

Since the earliest studies on phospholipids in aqueous disperson, (Bangham, A. D., M. M. Standish and J. C. Watkins, 1965, "Diffusion of Univalent Ions Across the Lamellae of Swollen Phospholipids", J. Mol. Biol. 13:238–252), pure lecithins have always been found in liposomal form, with an aqueous space contained by single or multiple continuous bilayers. This is true even for synthetic lecithins with complex thermal properties, such as dipalmitoyl phosphatidylcholine, which has at least three phase transitions (Chen, S. C., J. M. Sturtevant, and B. J. Gaffney, 1980, "Scanning Calorimetric Evidence for a Third Phase Transition in Phosphatidylcholine Bilayers", Proc. Natl, Acad. Sci. USA, 77:5060–5063). The phase transitions may change the bilayer spacings (Inoko, Y., and T. Mitsui, 1978, "Structural Parameters of Dipalmitoyl Phosphatidylcholine Lamellar Phases and Bilayer Phase Transitions", J. Physiol. Soc. Japan, 44:1918–1924), and also the surface areas of the liposomes (Yager, P., J. P. Sheridan and W. L. Peticolas, 1982, "Changes in Size and Shape of Liposomes Undergoing Chain Melting Transitions as Studied by Optical Microscopy", Biochim. Biophys. Acta. 693:485–491) (Evans, E. and R. Kwok, 1982, Mechanical Calorimetry of Large Dimyristoylphosphatidylcholine Vesicles in the Phase Transition Region, Biochemistry, 21:4874–4879), but the topology of the liposomes remains unchanged.

The lecithin, 1,2-bis(10,12-tricosadiynoyl)-sn-glycero-3-phosphocholine ($DC_{23}PC$), contains a diacetylenic group halfway down each of its 23-carbon hydrocarbon chains. This lecithin polymerizes to a rigid linear polyene via a 1–4 addition reaction if irradiated with 254 nm light. Radiation, such as gamma rays or high energy electrons, will also polymerize this lecithin (Wegner, G., 1969., 1969, Topochemische Reaktionen von "Monomeren Mit Konjugierten Driefachbondungen:, Z. Naturforsch, 24b:824–832).

The polymerization reaction only proceeds when the monomers are properly aligned, as in crystals, and not in the melt (Baughman, R. H. and R. R. Chance, 1978, Fully Conjugated Polymer Crystals: Solid State Synthesis and Properties of the Polydiacetylenes, Ann. NY Acad. Sci. 313:705–725). The polymer forms only when the lipid is below its phase transition temperature ($T_m$) of 40° C. (Johnston, D. S., S. Sanghera, M. Pons, and D. Chapman, 1980, Phospholipid Polymers: Synthesis and Spectral Characteristics", Biochim, Biophys. Acta. 602:57–69; O'Brien, D. F., T. H. Whiteisdes, and R. T. Klingbiel, 1981, The Photopolymerization of Lipid-Diacetylenes in Bimolecular-layer Membranes", J. Polym, Sci. Part B. 19:95–101: Lopez, E., D. F. O'Brien and T. H. Whitesides, 1982, "Structural Effects on the Photopolymerization of Bilayer Membranes", J. Am. Chem. Soc. 104:305–307): Leaver, J., A. Alonzo, A. A. Durrani, and D. Chapman, 1983, The Physical Properties and Photopolymerization of Diacetylene-Containing Phospholipid Liposomes", Biochim. Ciophys, Acts., 732:210–218. The polymer formed from the lipid $DC_{23}PC$ is dark red.

In prior work reported by the inventors using the polymerizable diacetylenic lecithin, it was found that the normal liposomes formed by gentle dispersion of the lipid above its phase transition temperature ($T_m$) became unstable and appeared to disintegrate on cooling through the transition point or temperature ($T_m$) (Yager, P., and P. E. Schoen, 1984, Formation of Tubules by a Polymerizable Surfactant, Mol. Cryst. Liq. Cryst. 106:371–381). The present inventors noted that the liposomes violently broke into small shards when the monomeric lipid was cooled rapidly to below 30° C., but, when the lipid was cooled slowly to 37° or 38° C., which is within the rather broad melting transition of the compound (DC23PC), the liposomes converted quantitatively to hollow tubes over a period of a minute. The tubules were between 0.3 microns and 1 micron in diameter, with fairly thin walls, and ranged in length from a few to hundreds of micrometers.

After polymerization, the tubules do not return to liposomal form when heated. Instead, the tubules exhibit thermochromism which indicates temperature effects on the conformation of the chromophoric polymer.

While phosphatidylcholines have been considered topologically inert, other classes of lipids, such as phosphatidylethanolamines, phosphatidylglycerol, cardiolipidin, and other charged lipids can convert to non-lamellar phases, such as the inverted hexagonal ($H_{II}$) phase (Cullis, P. R., and B. De Kruiff, 1979, "Lipid Polymorphism and the Functional Roles of Lipids in Biological Membranes, Biochim. Biophys, Acta, 559:399–420), or, in the case of phosphatidylserines in the presence of $Ca^{2+}$, a rolled-up lamellar phase dubbed cochleate cylinders (Papahadjopoulos, D., W. J. Vaiol, K. Jacobson, and G. Poste, 1975 "Cochleate Lipid Cylinders: Formation by Fusion of Unilamellar Lipid Vesicles, Biochim. Biophys. Acta. 394:483–491).

Structures somewhat similar to tubules were reported by Leaver, J. A., Alonzo, A., A. Durrani, and D. Chapman, for a diacetylenic lecithin with 20-carbon long fatty acid chains. Leaver et al. assumed the structure to be similar to cochleate cylinders, "The Physical Properties and Photopolymerization of Diacetylene-Containing Phospholipid Liposomes," Biochim. Biophys. Acta. 732:210–218, 1983. Tubules and cochleates are superficially similar, but previously reported electron microscopic studies on $DC_{23}PC$ by the inventors indicated that the tubules were somewhat different from cochleate cylinders because tubules are open ended and often consist of only a few bilayers (Yager, P. and P. E. Schoen, "Formation of Tubules by a Polymerizable Surfactant, Mol. Cryst. Liq. Cryst.," 106-371-381, 1984.

Cochleate cylinders are similar in diameter to tubules, but cochleate cylinders are not as long as tubules, and they consist of very tightly wrapped multibilayers with little or no internal aqueous space (Papahadjopoulos, D., W. J. Vail, K. Jacobson, and G. Poste, "Cochleate Lipid Cylinders; Formation by Fusion of Unilamellar Lipid Vesicles," Biochim. Biophys. Acta 394:483–491, 1975.

Recently, Nakashima, N., S. Asakuma, and T. Kunitake observed a tubular lipid structure formed from an amino-based surfactant, "Optical Microscopic Study of Helical Superstructures of Chiral Bilayer Membranes, J. Am. Chem. Soc., 107:509–510, 1985. The tubules described by Nakashima et al. are not polymerizable and so cannot be made stable or rugged. Moreover, the annealing time of these tubules is approximately a month.

The self-assembly of $DC_{23}PC$ into tubules has been observed by two distinctly different pathways. Yager and Schoen, two of the inventors, previously reported one method of thermal formation of tubules which results as a consequence of cooling liquid-crystalline large multilamellar vesicles or stacked bilayers sheets through a phase transition observed at approximately 39° C. "Molecular Crystals Liquid Crystals," 106:371–381, 1984.

The molecular characteristics and the polymorphic phase behavior of this lipid during the thermal formation of tubules has been characterized by vibrational spectroscopy and differential scanning calorimetry, Yager et al., Id, Rudolph et al, Biochem, Biophys. Acta, 902, 4347–359 (1987), Rudolph et al., Biophysical J. 51,185a; Burke et al., Biophysical J. 51, 185a.

Published articles suggest that fluid phase large multilamellar vesicles will form tubules directly upon cooling through the phase transition at 39°. It is also believed that fluid phase small unilamellar vesicles will form tubules when supercooled to 2° C., at which time they undergo a transition to a polymorphic, low temperature phase, stacked bilayer sheets.

The bilayer sheets are spectroscopically identical to the tubules. The sheets will form tubules if cycled through the transition at 39° C. This indicates that one requirement for thermal formation of tubules may be a high radius of curvature i.e. greater than one micrometer. The formation of stacked bilayer sheets from highly strained small unilamellar vesicles fulfills this requirement. In addition, it has been suggested by Yager et al., Biophysical J. 49, 320a (1986) that the mechanism of thermal tubule formation occurs by the wrapping or rolling of large multilamellar vesicles. This same mechanism could apply to the formation of tubules from stacked bilayer sheets.

Another method of tubule formation has been observed by Georger et al, J. Am. Chem. Soc., 109, p 6169 (1987), and is a result of spontaneous formation in mixed solvent systems. In this method, $DC_{23}PC$ is dissolved in ethanol and tubules are observed to form spontaneously upon the addition of water. The tubules formed from these two methods are morphologically similar and preliminary results on their molecular characteristics also indicate similarities.

Previous work by the inventors and their co-workers with 1,2-bis (10,12-tricosadiynoyl)-sn-glycero-3-phosphocholine ($DC_{23}PC$) discussed above, suggests making the tubules by slowly cooling the hydrated lipid to a point below 38° C. Almost all the reported work was done with only one compound $DC_{23}PC$.

In another work, the inventors and their co-workers tried to expand the process to other 1,2 bis alkadiynoyl-sn-glycero-3-phosphocholines. These compounds were found to form tubules if the hydrated lipid is cooled to a point a few degrees below its phase transition point ($T_m$). Singh, Price, Schnur, Schoen, and Yager, Tubule Formation by Heterobifunctional Polymerizable Lipids: Synthesis and Characterization. Abstract distributed at meeting August 1986. In another paper delivered at a meeting of the Indian Chemical Society in August of September 1986, the inventors and coworkers described work with isomers of diheptacosadiynoyl phosphocholines. An abstract was distributed at the meeting.

Suprisingly, when the slow cooling technique was applied to a broader range of diacetylenic phospholipids than just one, the process was found to be erratic. Some workers reported failure to produce tubules by the slow cooling process even with $DC_{23}PC$. The inventors work and work of others often found a high production of shards and other amorphous material when using the slow cooling process deserved in the literature $DC_{23}PC$. It has been found that this shrapnel production can be reduced by the improved methods of this invention.

SUMMARY OF THE INVENTION

It is therefore an object of the improved process of this invention to produce tubular structures from a broad variety of diacetylenic phospholipids. It is another object of the present invention to provide a method of producing tubules with a low amorphous material contamination. It is a further object of this invention to produce tubules of a relatively uniform length for each lipid variety from a broad variety of diacetylenic phospholipids. An additional object of this invention is to produce tubules in good yield for any diacetylenic phospholipid.

These and other objects of the invention are accomplished by hydrating the diacetylenic phospholipids above its endothermic transition temperature ($T_{mn}$) and subsequently cooling the hydrated lipid to a formation temperature below the lipids' exothermic transition temperature ($T_{mx}$). The formation temperature is held for a time sufficient to permit tubule structure formation.

This and other objects, advantages, and novel features of the present invention will become apparent from the following detailed description of the invention.

BRIEF DESCRIPTION OF THE DRAWINGS

The invention will be better understood by reference to the following drawings wherein.

DETAILED DESCRIPTION OF THE INVENTION

Figure 1:
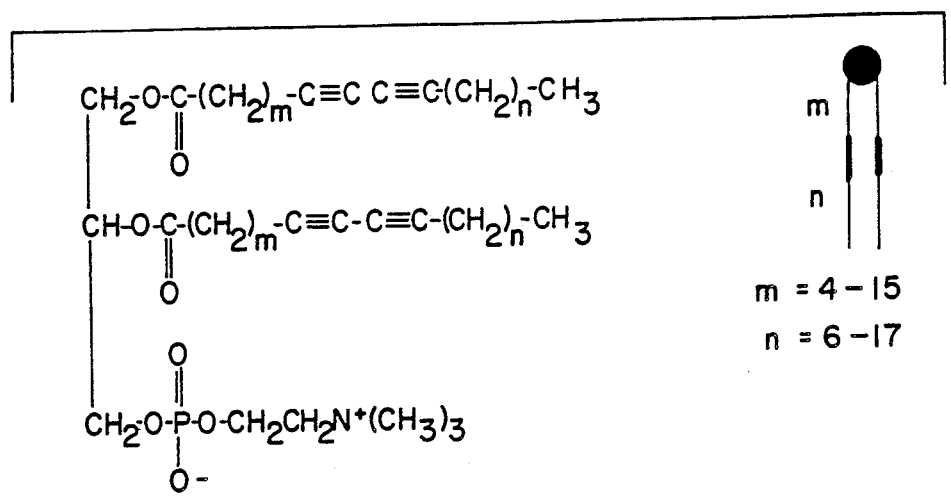
FIG. 1 is a chemical formula of the (m,n) $DC_{27}PC$ isomer series.

Chiral phosphatidylcholines with two hydrocarbon chains of 15 to 29 carbons having a diacetylene group at positions about the center of each chain or a mixture of these chiral phosphatidylcholines and other lipids are the preferred diacetylenic lipids of this invention as illustrated in FIG. 1. These diacetylenic phospholipids include 1,2-bis (10,12-tricosadiynoyl)-sn-glycero-3-phosphocholine ($DC_{23}PC$), 1,2-bis (10,12 hencosadiynoyl))-sn—glycero-3-phosphocholine ($DC_{21}PC$), 1,2-bis (11,13 heptacosadiynoyl)-sn-glycero-3-phosphocholine ($DC_{27}PC$), 1,2-bis (9,11-heptacosadiynoyl)-sn-glycero-3-phosphocholine, 1,2 (8,10 heptacosadiynoyl)sn-glycero-3-phosphocholine, and 1,2-bis (7,9 heptacosadiynoyl)sn-glycero-3-phosphocholine.

Generally the diacetylenic phosphocholine lipids are prepared by the general methods described in published articles, Singh et al. Synth. Commun. (16(7)847(1986 and Yager et al. Biophysical Journal Vol. 48, pp. 899–906(1985). After purification and drying the tubules is formed by first hydrating the diacetylenic phospholipid at about 10° C. above its endothermic transition point. Second, the lipid mixture is cooled slowly at a rate not to exceed 1° C. per minute, preferably not greater than 0.5° C. per min to a formation temperature 1° to 10° below the lipids' exothermic transition temperature. Preferably the formation temperature is 2–5° below the transition temperature. The solution is held at the formation temperature for between 30 minutes and 2 hours, most preferably 1 hour. Once the tubule structures are formed they are stable as long as the tubule structures are not heated above the endothermic transition temperature. If desired, the tubule structures can be polymerized by any of the well known means to a permanent tubule form.

Now having generally described the invention, the following specific examples illustrate specific applications of the invention.

EXAMPLE I

The fatty acid 10,12 tricosadiynoic acid is synthesized and the isomerically pure phospholipid 1,2-bis (10,12-tricosadiynoyl)-sn—glycero-3-phosphocholine ($DC_{23}PC$) derived from this fatty acid is esterified. The purified lipid can be procured from Avanti Polar Lipids. The phosphatidylcholine gives a single spot by thin layer chromatography. To form the tubule, the chloroform solution of the lipid is dried in vacuum then dispersed in filtered, deionized water with agitation at a temperature above 50° C.

The liposomes are slowly cooled at a rate of 1° per minute preferably to a formation temperature below the exothermic transition temperature. For DC 23 PC the transition temperature $T_{mx}$ is approximately 37° C. to 38° C. Typically, a temperature range 1–5° C. below the exothermic transition temperature is preferred. The temperature is maintained for about 1 hour. As the temperature is lowered the liposomes spontaneously roll up to form lipid tubule structures. The resulting tubule structures for $DC_{23}PC$ are from 5–500 micrometers long and have diameters from 0.5 to 1.0 micrometers.

The tubule structures produced can be polymerized to make them mechanically, thermally, and chemically more rugged. To fix the form of the tubules they can be polymerized by exposure to a Spectroline mercury vapor lamp or any suitable method which initiates the 1-4 diacetylene addition reaction. Chemical polymerization and irradiation are preferred with UV light or gamma ray irradiation being most preferred.

The topotactic polymerization of diacetylenes requires accurate alignment of the monomers, so that such reactions do not proceed in the melt (Baughman et al., Ann. New York Acad. Sci., 705 (1978)). Recent studies on phospholipids in which one or more of the hydrocarbon chains contain diacetylenic units have shown that the production of red polymer occurs below the hydrocarbon chain melting transitions of such systems. Lopez et al., J. Am. Chem. Soc. 104, 305 (1982). See also, Pons et al., J. Ply. Sci. Polym. Chem. Ed. 20, 513 (1982). See also, Johnston et al., Biochem. 22, 3194 (1983).

Calorimetric studies are performed on a Perkin-Elmer DSC-7, and spectrophotometry on a Cary 219C. Optical microscopy can be performed with a Leitz Ortholux I microscope outfitted with long working distance objectives for phase and interference contrast. Temperature of the samples for optical microscopy is controlled by a Bailey TS-2ER heating and cooling stage. Samples for electron microscopy are frozen from room temperature by rapid immersion in Freon 22 at its melting point. Fracturing and replication is done at −105° C. in a Balzers 301 Freeze Fracture device, and replicas are photographed in a Philips 200 transmission electron microscope.

The introduction of polymerizable phospholipids into the structure provides a method for stabilizing the structure. Structures of interest can be formed from the monomers and then ruggedized by polymerization.

Tubules can be formed with a broad range of diacetylinic phosphocholines. Positional isomers of a preferred bis 27hydrocarbon chain phosphocholine ($DC_{27}PC$) are prepared as follows:

EXAMPLE 2

Synthesis of Diacetylenic Acids: The positional isomers of diacetylenic acids are synthesized by coupling the appropriate ω-alkynoic acids with iodoalkynes using the procedure reported by Singh and Schnur, Synth. Commun., 16(7) 847 (1986). The ω-alkynoic acids are prepared by reacting the bromo analog of the acid with lithium acetylideethyenediamine complex at room temperature. The acids are purified by column chromatography on silica gel (chloroform as eluting solvent) followed by crystallization with hexanes. All the acids are characterized by infrared spectroscopy (Perkin Elmer FTIR 1800), nuclear magnetic resonance, melting point, thin layer chromatography, mass spectrometry, and elemental analysis. These acids are then converted into their anhydrides by reacting with 0.55 mole equivalent dicyclohexyl carbodiimide in methylene chloride, and stored in the dark at room temperature.

Synthesis of 1,2 bis heptacosadiynoyl-sn-glycero-3-phosphocholine: $DC_{27}PC$ is synthesized by reacting the appropriate diactylenic acid with the L-alpha glycerophosphorylcholine derived from egg lechithin (Avanti Polar lipids, Birmingham, Ala.) The phospholipids are purified by column chromatography on silica gel followed by acetone precipitation. Their purity is monitored using a chloroform:methanol:water (65:25:4) solvent system and is characterized by infrared spectroscopy and nuclear magnetic resonance. The molecular weight of the lipid is obtained by negative ion fast atom bombardment mass spectroscopy. The lipids are stored as polycrystalline powders after filtering a methylene chloride solution through sintered glass.

FIG. 1 shows the positional isomers of $DC_{27}PC$ in which $m+n=21$. These represent isomers with diacetylenes close to the interfacial region and isomers with the diacetylenic group near the terminal methyl group. The nomenclature employed identifies the m portion of the alkyl chain, that is, the portion between the diacetylenic group and the carbon backbone (above) and the n portion between the diacetylene and the methyl end of the chain (below). For instance, (4,17) $DC_{27}PC$ identifies the isomer with alkyl chains that have 4 methylenes above the diacetylene and 17 methylenes below the diacetylene.

Calorimetric characterization of $DC_{27}PC$: A Perkin-Elmer DSC-7 is used to generate all of the calorimetric scans. Transition temperatures of the dry polycrystalline material are generated by lyophilizing aliquots of $DC_{27}PC$ previously dried down from chloroform and stored in a vacuum dessicator. These samples are opened in a dry box and purged with dry nitrogen.

2-5 mg. of material is loaded into a stainless steel DSC pan. This procedure is used in the preparation of DPPC to qualitatively determine the amount of water present in these samples. Using this procedure, a transition temperature of 82° C. is obtained for dry DPPC. This is good agreement with Chapman et al. for the transition temperature of DPPC dihydrate polycrystalline powder, Chem. Phys. Lipids 1, 445 (1967).

These samples are cycled on the DSC at 1° C./min. until consecutive scans are repeatable. Lipid weights are determined from the known weight of the pan before and after introduction of the sample.

For hydrated transition temperatures, a film of $DC_{27}PC$ is made in the DSC pan by loading small aliquots of lipid in chloroform at 60° C. and drying over a stream of dry nitrogen. Residual solvent is removed by placing the pan in a vacuum dessicator for 24 hours. The pan is weighed to determine the weight of the lipid. Triple distilled, deionized water is then added to the pan just before being hermetically sealed. The concentration of lipid in the pan is usually between 50-100 mg./ml. The sample is held at 70° C. for at least an hour to ensure good hydration. Each sample is then cooled slowly to a formation temperature 1° C. below the $T_{mx}$ at 1° C./min. Slow cooling is necessary as more rapid cooling results in the formation of incompletely formed tubules, or shards.

After one cooling scan, the pan is opened and the sample is examined with light microscopy for the presence of tubule structures. Duplicate samples of each positional isomer are run in a similar manner with repeated cycling to determine the reversible, repeatable transition temperatures and accurate enthalpies.

Preparation of Tubules for FTIR spectroscopy: Tubules are prepared by hydrating polycrystalline powder (50 mg./ml.) at 10° C. above the hydrated transition temperature of the lipid (approximately 70° C) for at least one hour. This multilamellar suspension is then sonicated to clarity and cooled slowly at a rate or 1° C.. per minute to 5° C. preferably 2° below the exothermic transition temperature ($T_{mx}$) or gel phase transition point. The temperature is maintained for about 1 hour; a time sufficient to form tubule structures.

The sample is checked for the formation of tubule structures with light microscopy. A small aliquot is then loaded onto $BaF_2$ crystals with a TEFLON ® micron spacer in a sealed demountable cell. This cell is temperature controlled by mounting it on an aluminum water jacket which is then placed in the infrared spectrometer. All spectra are taken with a Perkin-Elmer FTIR 1800. Spectra are collected with 2 $cm^{-1}$ resolution and 500 scans coadded using triangular apodisation.

Figure 2:
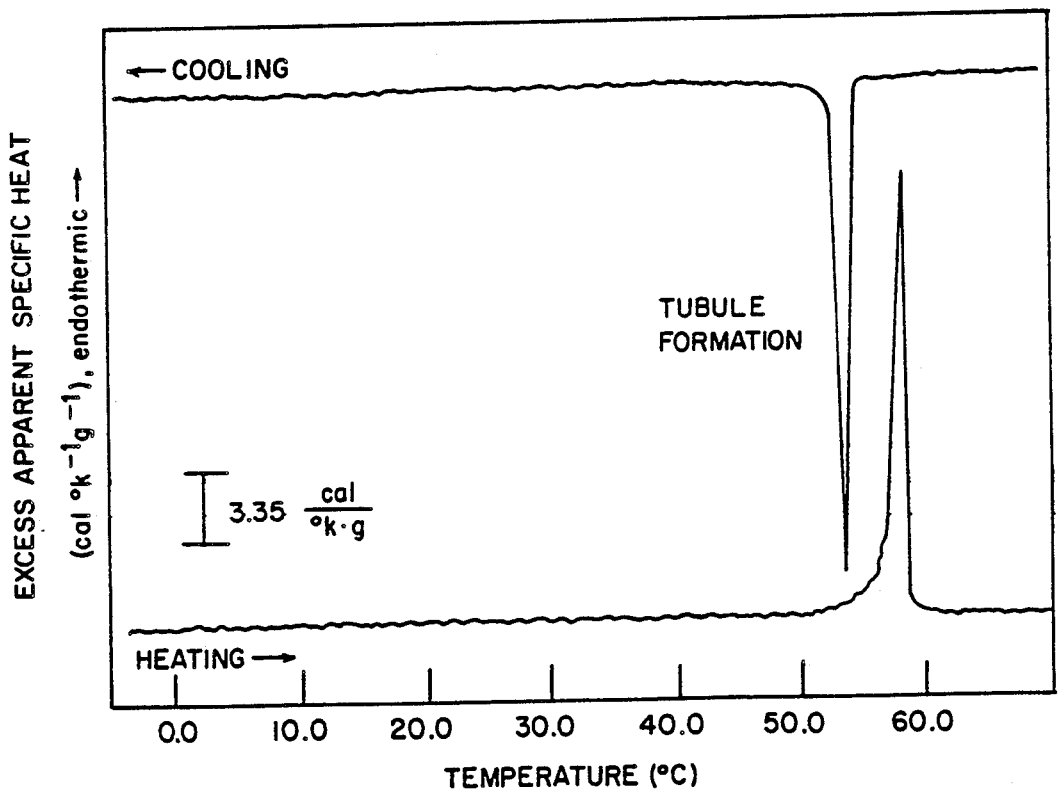
FIG. 2 shows differential scanning calorimetric traces of the cooling of multilamellar vesicles of (9,12) $DC_{27}PC$ to form tubule structures and the subsequent heating of the tubule structure suspension. Scan Rate is 1° C./min for both the heating and cooling scan.

FIG. 2 shows a typical calorimetric scan for the positional isomer (9,12) $DC_{27}PC$. The cycle is begun with samples above their endothermic phase transition temperature. As slow cooling progresses, these samples undergo a liquid-crystalline to gel phase transition that results in tubule structure formation. In (9,12) $DC_{27}PC$ the exothermic transition is observed at 52.3° C. with an enthalpy of 26 Kcal/mol. Subsequent heating of this sample reveals an endotherm ($T_{mn}$) at 55.9° C. with the same enthalpy as the exothermic transition.

Examination of the enthalpies of the transitions for all members of the isomer series shows that the enthalpy for the endotherm and exotherm for an individual isomer of the series are almost identical. In addition, there appears to be no apparent trend in the enthalpy of the transition as the diacetylene is moved down the alkyl chain.

Figure 3:
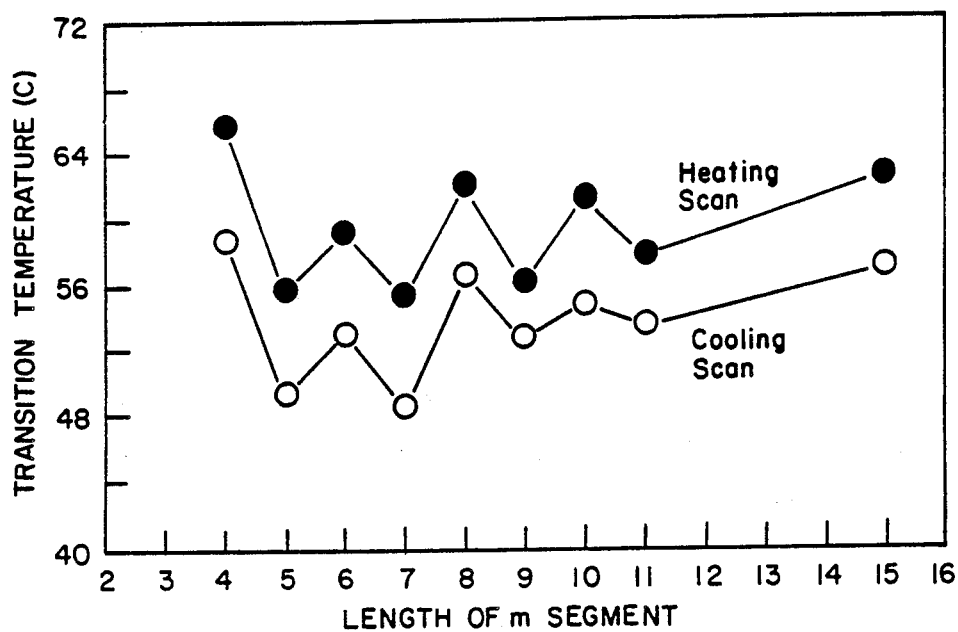
FIG. 3 shows the effect of length of m segment on the endothermic and exothermic transition temperatures of varying members of the $DC_{27}PC$ isomer series.

FIG. 3 shows the transition temperatures of the cooling scans (tubule structure formation) and heating scans of cycling multilamellar preparations of hydrated positional isomers of $DC_{27}PC$ as a function of the length of the m segment. Of course, for an increase in m, there is a corresponding decrease in n. For a 27 carbon lipid $m+n=21$.

The results shown in FIG. 3 indicate that there is a periodic alternation in both the endothermic and exothermic phase transition temperatures as the diacetylene is moved down the alkyl chain. For example, (5,16) $DC_{27}PC$ has a gel to liquid crystalline $T_{mx}$ at 55.4° C., while the $T_{mx}$ for (6,15) $DC_{27}PC$ is 58.9° C. Moving the diacetylene one position further along the alkyl chain results in a shift of the $T_{mx}$ to 54.9° C., for (7,14) $DC_{27}PC$.

These results reveal that odd numbered m segments have consistently lower transition temperatures in both the heating and cooling scans. In addition, there is a constant hysteresis between the heating and cooling scans. The hysteresis observed in these calorimetric results is repeatable. There was no observed trend in the enthalpies of these transition as the enthalpy of the endothermic transition varied between 26 Kcal/mol. and 29 Kcal/mol.

The melting behavior of positional isomers of lecithins with double bonds indicate that as the double bond is moved toward the middle of the chain, the transition temperature is lowered, rising again as the double bond is moved toward the terminal methyl, Small, Phys. Chemistry of Lipids, pp 475–522, Plenum Press, NY (1986). In addition, the cis isomers of olefinic fatty acids and lipids display this effect with greater intensity than the trans isomer, presumably due to the increased gauche conformers that are dictated by the 120° angle with respect to the chain axis introduced by the cis double bond. Alternating melting behavior is also observed in both the cis and trans olefinic fatty acids, with the even position olefins having higher melting temperatures. This odd-even effect is not observed in the corresponding phospholipids such as cis-unsaturated dioctadecanoic phosphatidylcholines (18,20).

There is no marked trend observed in the transition temperatures of the positional isomers of $DC_{27}PC$. Acetylenic groups have the same angle with respect to the chain as the c—c—c angle of a polymethylene chain, and the degree of disorder introduced is thus not as great as in the cisolefins. No significant decrease is observed in the transition temperature of $DC_{27}PC$ isomers with the diacetylenic groups in the middle of the alkyl chain. As the diacetylene is moved toward the head group however, the transition temperature is raised slightly, in agreement with the behavior of acetylenic fatty acids. It is interesting to note that the enthalpy of the endothermic and exothermic transitions are identical indicating that the enthalpy for tubule formation, as distinct from hydrocarbon chain freezing, is negligible. The persistence of odd-even effects in the $DC_{27}PC$ series may indicate that the chain segments are decoupled by the diacetylene and that the individual m and n segments are quite ordered. This may indicate that the acyl chains of $DC_{27}PC$ are behaving like two segments of straight chain alkanes (m and n), as odd-even effects are observed in these systems. Raman and infrared spectroscopic studies of $DC_{27}PC$ have suggested that the two portions of the chains separated by the diacetylene are highly ordered and vibrationally uncoupled.

Figure 5:
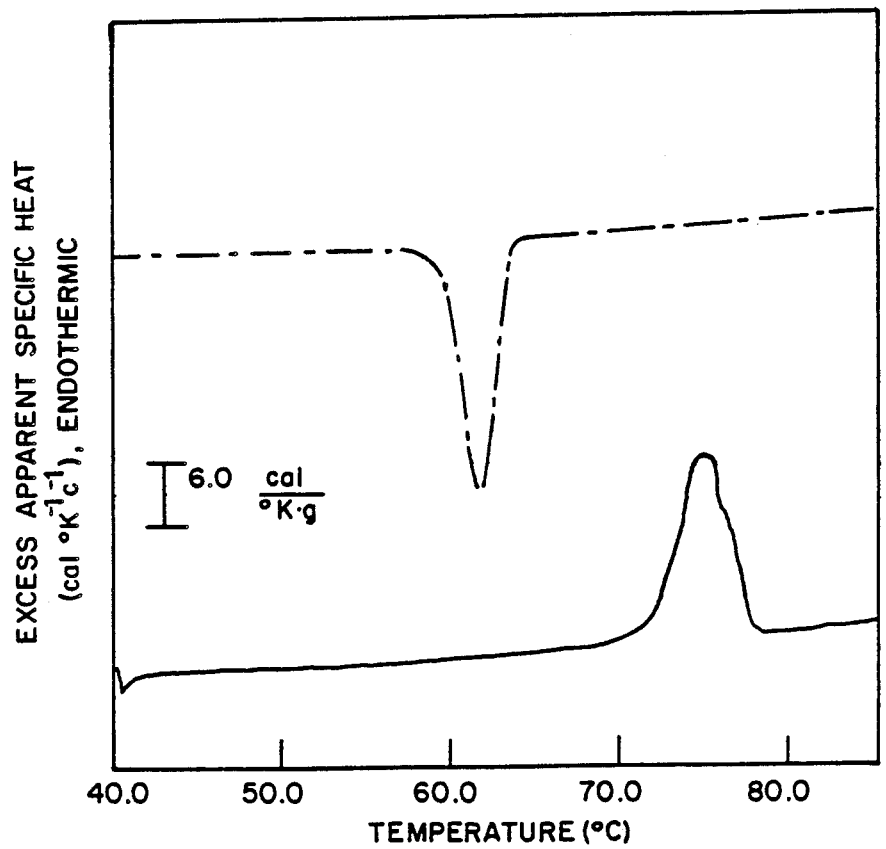
FIG. 5 is Calorimetric scans of cooling and heating of dry polyscystalline (4,17) $DC_{27}PC$. Scan rate is 1° C./min for heating and cooling.
Figure 4B:
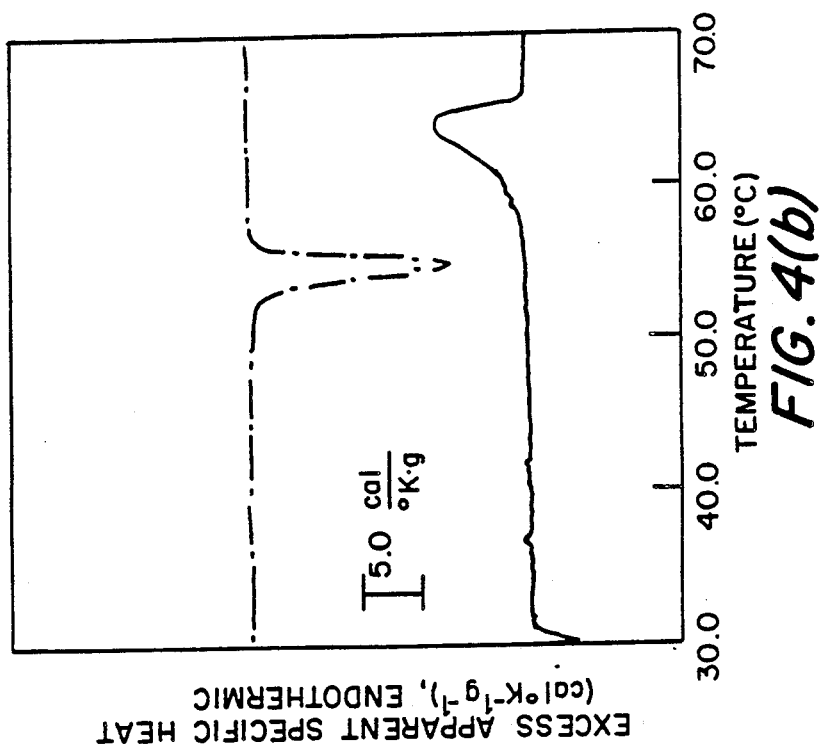
FIG. 4 is (a) Calorimetric scans of cooling hydrated (15,6) $DC_{27}PC$ multilamellar vesicles to form tubules, with subsequent heating of the tubule structure suspension and FIG. 4 (b) is calorimetric scans of the cooling and heating of polycrystalline (15,6) $DC_{27}PC$. All scan rates are 1° C./min.
Figure 4A:
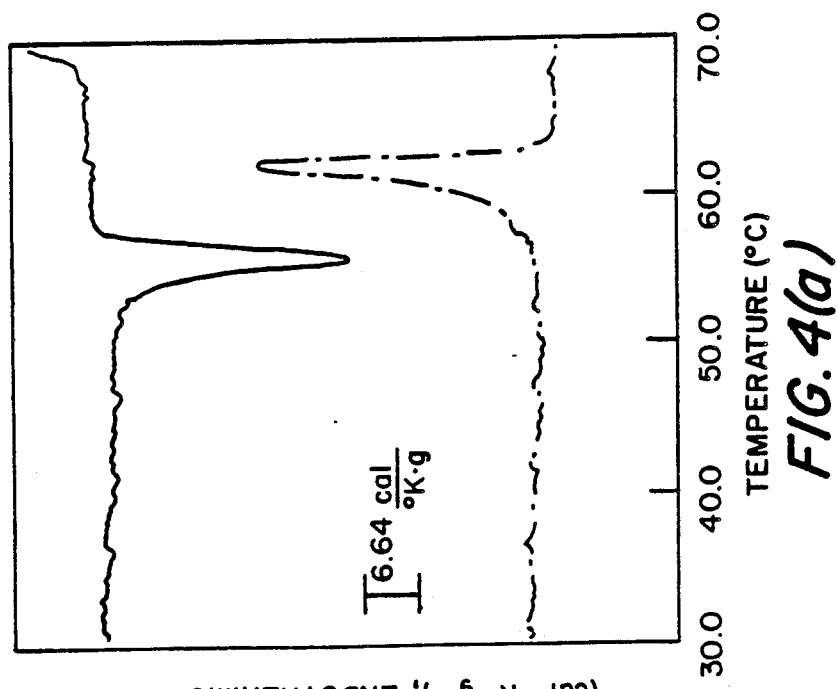

The phase properties of hydrated and dry polycrystalline powder of 15,6 $DC_{27}PC$ is presented in the calorimetric scans in FIG. 4a and 4b, respectively. Dry polycrystalline 15,6 $DC_{27}PC$ material has a endothermic transition temperature of 63.7° C. (enthalpy=29 Kcal/mol.). Dry (4,17) has an endothermic transition at 74.8° C. (enthalpy=30 Kcal/mol.) with an exotherm observed at 61.5° C. (enthalpy=28 Kcal/mol.) upon slow cooling (FIG. 5). The endothermic transition observed for hydrated (4,17) $DC_{27}PC$ is 66.4° C. and 58.9° C. for the hydrated exothermic transition (see FIG. 3).

The hysteresis observed in the hydrated scans of these lipids is also present in the dry phase behavior. The enthalpy associated with the endothermic transition was slightly higher in every member of the isomer series. In addition, the enthalpies of the dry transitions were slightly higher (1–2 Kcal/mol) than the corresponding hydrated transitions.

The formation of tubules by slow cooling to a point below the gel or exothermic transition temperature corrects the erratic results experienced by prior reports where temperatures were reduced to a transition temperature which was the same as the exothermic transition temperature. It is important in this process to reduce the temperature slowly at a rate not greater than 1° C. per min. preferably 0.5° C. through the exothermic transition temperature to a formation temperature 1°–10° C., preferably 2°–5° C. below the exothermic transition temperature also known as the gel phase transition. This processing technique is applicable to the family of diacetylenic phosphocholines.

The tubules formed are usually extremely straight hollow cylinders of approximately 0.5 micrometers diameter and 5 to 100 micrometers in length. These tubules can be used in a vast variety of ways. The tubules can be used to hold materials in a manner well known for lipid vesicles described above. In addition, the tubules can be coated with metals as described in co-pending application Ser. No. 063,029 filed June 16, 1987 now U.S. Pat. No. 4,911,981.

Obviously many modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A method of forming tubules relatively free from amorphous material from diacetylinic phosphocholines having hydrocarbon chains of 15 to 29 carbons each comprising the steps of:

hydrating a diacetylinic phosphocholine crystalline, lipid powder above its endothermic transition temperature;

cooling said hydrated lipid at a rate not exceeding 1° per minute to a formation temperature 1° to 10° C. below the exothermic transition temperature; and holding said formation temperature for 30 minutes to 2 hours to form tubule structures.

2. The method of claim 1 wherein the hydrated lipid is cooled at a rate of 0.5° C. per 1° C. per minute.

3. The method of claim 2 wherein the formation temperature is 1° C. to 5° C. below the exothermic transition temperature.

4. The method according to claim 2 wherein the formation temperature is maintained for about 1 hour.

5. The method of claim 4 wherein the tubule structure is polymerized to a permanent form.

6. The method of claim 5 wherein the lipid is 1,2-bis(10,12 heptacosadiynoyl)-sn-glycero-3-phosphocholine.

7. The method of claim 4 wherein the diacetylinic phosphocholine lipid has at least 27 carbons in each hydrocarbon chain.

8. The method of claim 7 wherein the lipid is 1,2-bis(11,13 heptacosadiynoyl)-sn-glycero-3-phosphocholine.

9. The method of claim 7 wherein the lipid is 1,2-bis (9,11 heptacosadiynoyl)-sn-glycero-3-phosphocholine.

10. The method of claim 7 wherein the lipid 1,2 (8,10 heptacosadiynoyl)-sn-glycero-3-phosphocholine.

11. The method of claim 7 wherein the lipid is 1,2-bis (7,9 heptacosadiynoyl)-sn-glycero-3-phosphocholine.

12. The method of claim 7 wherein the tubule structure is polymerized to a permanent form.

* * * * *